United States Patent [19]

Springer et al.

[11] Patent Number: 5,010,180
[45] Date of Patent: Apr. 23, 1991

[54] WATER-SOLUBLE AZO COMPOUNDS HAVING A N-(PHENETHYL)-AMIDO-CARBONYL-METHOXYPHENYL RADICAL, SUBSTITUTED BY A FIBER-REACTIVE GROUP OF THE VINYLSULFONE SERIES, SUITABLE AS FIBER-REACTIVE DYESTUFFS

[75] Inventors: Hartmut Springer, Königstein/Taunus; Uwe Reiher, Frankfurt am Main, both of Fed. Rep. of Germany

[73] Assignee: Hoechst Aktiengesellschaft, Frankfurt, Fed. Rep. of Germany

[21] Appl. No.: 473,620

[22] Filed: Feb. 1, 1990

[30] Foreign Application Priority Data

Feb. 3, 1989 [DE] Fed. Rep. of Germany ....... 3903224

[51] Int. Cl.$^5$ .................... C09B 62/085; C09B 62/51; C09B 62/513; D06P 1/384
[52] U.S. Cl. .................................. 534/638; 534/582; 534/637; 534/642; 534/887; 564/163; 564/166
[58] Field of Search ................ 534/632, 638, 642, 637

[56] References Cited

· U.S. PATENT DOCUMENTS 3,184,280 5/1965 Zerweck et al. ............... 534/642 X

OTHER PUBLICATIONS

Solov'eva et al., *Chemical Abstracts*, vol. 70, No. 28585p(1969).

*Primary Examiner*—Floyd D. Higel
*Assistant Examiner*—Fiona T. Powers

[57] ABSTRACT

Water-soluble azo compounds corresponding to the general formula D—N=N—K which have advantageous fiber-reactive dyestuff properties and dye materials containing carboxamide groups and in particular materials containing hydroxy groups, such as wool and in particular cellulose fiber materials, in deep fast shades are described.

In the formula D—N=N—K:
D is a radical of the general formula

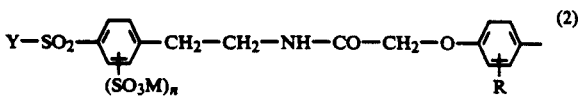

in which Y is the vinyl group or an ethyl group in the β-position which can be removed by an alkaline radical, R is hydrogen, nitro, lower alkyl, lower alkoxy, carboxy or hydroxy or halogen, M is hydrogen or a salt-forming metal atom and n is the number zero or 1; and K is a radical of a water-soluble coupling component which can be coupled in one position and can also contain an azo group, or the radical of a water-soluble coupling component which can be coupled in two positions, in each case from the series comprising aminobenzenes, phenols, naphthols, aminonaphthols, acylamino-napthols, dihydroxynaphthalenesulfonic acids, phenylazo-aminonaphtholsulfonic acids, naphthylazo-aminoaphtholsulfonic acids, 5-pyrazolones, 5-aminopyrazoles, acetoacetyl arylides, 2-hydroxy-6-pyridones and hydroxyquinolines, it also being possible for K to contain one or more fiber-reactive groups, in addition to the substituents customary in dyestuffs.

Precursors of these azo compounds of the general formula

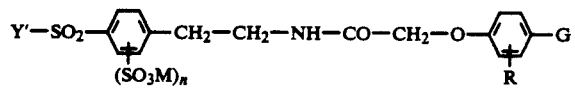

in which G is the amino or nitro group, R, M and n have the abovementioned meanings and Y' is the β-hyroxyethyl group or has one of the abovementioned meanings for Y are furthermore described.

12 Claims, No Drawings

WATER-SOLUBLE AZO COMPOUNDS HAVING A N-(PHENETHYL)-AMIDO-CARBONYL-METHOXYPHENYL RADICAL, SUBSTITUTED BY A FIBER-REACTIVE GROUP OF THE VINYLSULFONE SERIES, SUITABLE AS FIBER-REACTIVE DYESTUFFS

DESCRIPTION

The present invention relates to the field of fiber-reactive dyestuffs.

Novel water-soluble azo compounds corresponding to the general formula (1)

which have useful fiber-reactive dyestuff properties have been found.

In this formula (1):

D is a radical of the general formula (2)

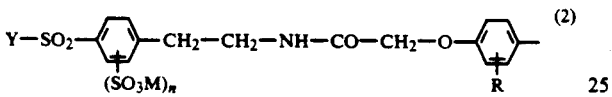

in which

Y is the vinyl group or a group of the general formula (3)

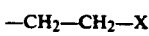

in which

X is a substituent, which can be eliminated by an alkali to form the vinyl group, R is a hydrogen atom, a nitro group, an alkyl group having 1 to 4 carbon atoms, such as an ethyl or in particular methyl group, an alkoxy group having 1 to 4 carbon atoms, such as an ethoxy or in particular methoxy group, a carboxy group, a hydroxy group or a halogen atom, such as a chlorine or bromine atom, but preferably a hydrogen atom, n represents the number zero or 1, preferably zero (and in the case where n=zero, the group is a hydrogen atom) and M is a hydrogen atom or a salt-forming metal atom, such as, in particular, an alkali metal atom, such as, for example, sodium, potassium or lithium;

K is a radical of a water-soluble coupling component which can be coupled in one position and can also contain an azo group, or the radical of a water-soluble coupling component which can be coupled in two positions, in each case from the series comprising aminobenzenes, phenols, in particular sulfonic acids and carboxylic acids thereof, naphthols, in particular sulfonic acids and carboxylic acids thereof, aminonaphthols, in particular sulfonic acids thereof, and acylamino-naphthols, in particular sulfonic acids thereof, with the acyl radical of an alkane- or alkenecarboxylic acid having in each case 1 to 4 or 2 to 4 carbon atoms in the alkyl or alkenyl radical respectively, or of an aromatic carboxylic acid, such as benzoic acid, or of an aromatic sulfonic acid, such as benzene- or toluenesulfonic acid, or of an N-substituted carbamic acid, such as the N-phenylureido radical, or from the series comprising dihydroxynaphthalenesulfonic acids, phenylazo- and naphthylazo-aminonaphtholsulfonic acids, 5-pyrazolones and 5-aminopyrazoles, acetoacetyl arylides, 2-hydroxy-6-pyridones and hydroxyquinolines, it also being possible for K to contain, in addition to the substituents customary in dyestuffs, one or more fiber-reactive groups, such as, for example, a group —SO$_2$—Y, where Y has the above meaning, or a 4-fluoro- or 4-chloro-6-amino-s-triazin-2-ylamino group, the amino group of which in the 6-position can be mono- or disubstituted by alkyl having 1 to 4 carbon atoms and/or phenyl, it being possible for the phenyl radical to be substituted by substituents from the group comprising sulfo, carboxy, methoxy, ethoxy, methyl, chlorine, bromine and —SO$_2$—Y, where Y has the above meaning.

Examples of substituents X which can be removed under alkaline conditions are halogen atoms, such as the bromine atom and chlorine atom, ester groups of organic carboxylic and sulfonic acids, such as an alkanoyloxy radical having 2 to 5 carbon atoms, for example the acetyloxy group, or a sulfobenzoyloxy, benzoyloxy, phenylsulfonyloxy or toluylsulfonyloxy radical, and moreover, for example, the acid ester groups of phosphoric acid, sulfuric acid and thiosulfuric acid (phosphato or sulfato or thiosulfato groups), as well as dialkylamino groups with alkyl groups having in each case 1 to 4 carbon atoms, such as the dimethylamino and diethylamino group.

Preferably, Y is the vinyl group and in particular the β-sulfatoethyl group.

Sulfo groups are groups corresponding to the general formula —SO$_3$M, carboxy groups are groups corresponding to the general formula —COOM, sulfato groups are groups corresponding to the general formula —OSO$_3$M, phosphono groups are groups of the general formula —PO$_3$M$_2$, thiosulfato groups are groups corresponding to the general formula —S—SO$_3$M and phosphato groups are groups corresponding to the general formula —OPO$_3$M$_2$, in which M has the abovementioned meaning.

Of the compounds of the general formula (1) according to the invention, those compounds in which K is a radical of the following formula (4a), (4b), (4c), (4d), (4e), (4f), (4g), (4h), (4i), (4k), (4m), (4n), (4p), (4q), (4r), (4s), (4t) (4v) or (4w) can be singled out as an example:

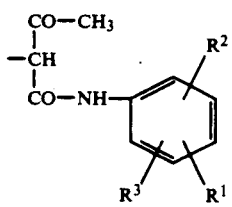

(4a)

-continued
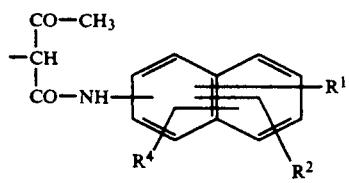 (4b)
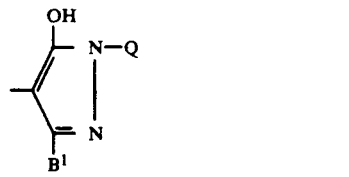 (4c)
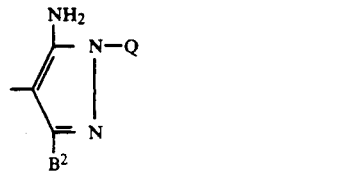 (4d)
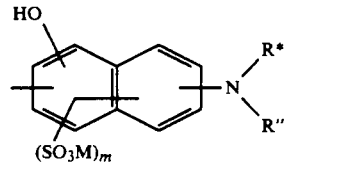 (4e)
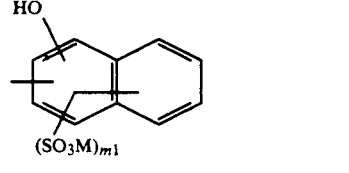 (4f)
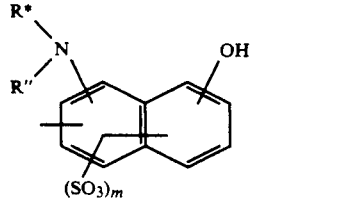 (4g)
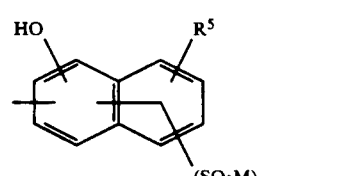 (4h)
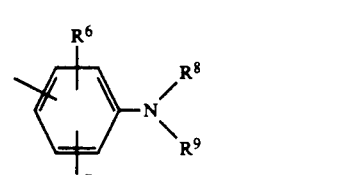 (4i)
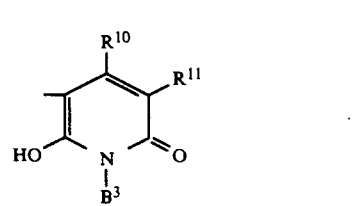 (4k)

-continued
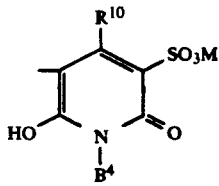
(4m)
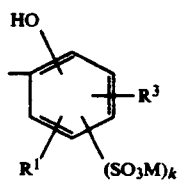
(4n)
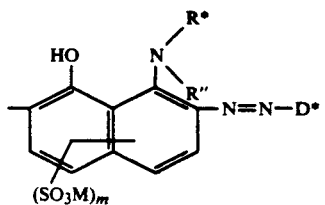
(4p)
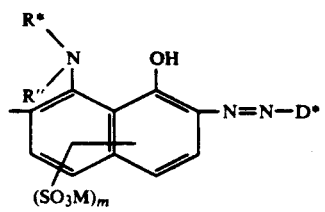
(4q)
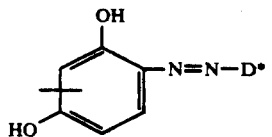
(4r)
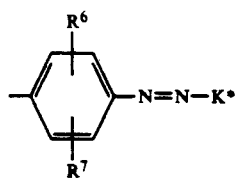
(4s)
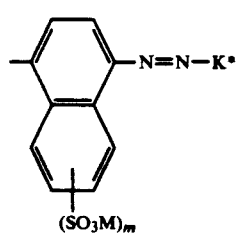
(4t)
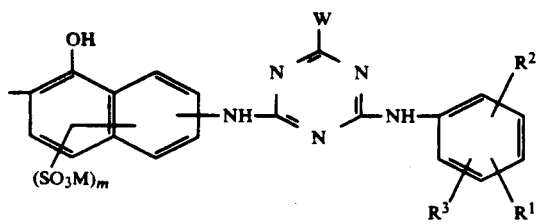
(4v)

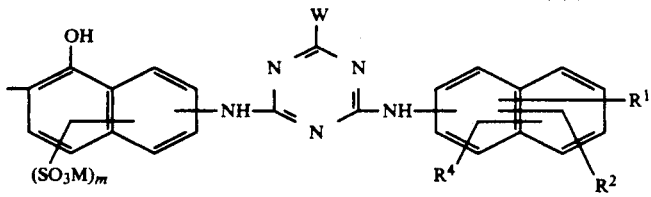
(4w)

In these formulae:

$R^1$ is a hydrogen atom or a carboxy or sulfo group or a group of the general formula —$SO_2$—Y, where Y has the above meaning;

$R^2$ is a hydrogen atom, an alkyl group having 1 to 4 carbon atoms, such as, in particular, a methyl or ethyl group, an alkoxy group having 1 to 4 carbon atoms, such as, in particular, a methoxy or ethoxy group, a chlorine or bromine atom or a carboxy, sulfo or nitro group;

$R^3$ is a hydrogen atom, an alkyl group having 1 to 4 carbon atoms, such as, in particular, the methyl or ethyl group, an alkoxy group having 1 to 4 carbon atoms, such as, in particular, the methoxy or ethoxy group, or a chlorine or bromine atom;

$R^4$ is a hydrogen atom or a sulfo or carboxy group, preferably a hydrogen atom if $R^1$ is a group —$SO_2$—Y;

$B^1$ is an alkyl group having 1 to 4 carbon atoms, such as, in particular, the methyl group, a carboxy group, a carbalkoxy group having 2 to 5 carbon atoms, the carbamoyl group or a phenyl radical which is optionally substituted by sulfo, carboxy, methyl, ethyl, methoxy, ethoxy and/or chlorine;

$B^2$ is an alkyl group having 1 to 4 carbon atoms, such as, in particular, the methyl group, a carboxy group, a carbalkoxy group having 2 to 5 carbon atoms, the carbamoyl group or a phenyl radical, which can be substituted by 1 to 2 substituents from the group comprising alkyl having 1 to 4 carbon atoms, alkoxy having 1 to 4 carbon atoms, chlorine, bromine and sulfo;

Q is a phenyl radical, which can be substituted, such as, for example, by 1, 2 or 3, preferably 1 or 2, substituents from the group comprising chlorine, bromine, methyl, ethyl, methoxy, ethoxy, carboxy, sulfo and alkanoylamino, such as acetylamino, and/or by a group of the general formula —$SO_2$—Y, where Y has the abovementioned meaning, or is a naphthyl radical, which can be substituted by 1, 2 or 3 sulfo groups and optionally by an alkyl group having 1 to 4 carbon atoms, an alkoxy group having 1 to 4 carbon atoms, a chlorine atom or an alkanoylamino group having 2 to 5 carbon atoms, and/or by a group of the general formula —$SO_2$—Y, where Y has the abovementioned meaning;

R* is a hydrogen atom or an alkyl group having 1 to 4 carbon atoms, which can be substituted by a phenyl radical or a phenyl radical which is substituted by sulfo and/or —$SO_2$—Y, where Y has the above meaning;

R" is a hydrogen atom or an alkyl group having 1 to 4 carbon atoms, which can be substituted by a phenyl radical or a group of the formula —$SO_2$—Y, where Y has the above meaning, or is a phenyl radical, which can be substituted by 1 or 2 substituents from the group comprising alkyl having 1 to 4 carbon atoms, alkoxy having 1 to 4 carbon atoms, chlorine, bromine, sulfo and —$SO_2$—Y, where Y has the above meaning;

$R^5$ is the phenylureido group, the phenyl radical of which can be substituted by a group of the formula —$SO_2$Y, where Y has the above meaning, or is an alkanoylamino group having 2 to 5 carbon atoms, such as the acetylamino or propionylamino group, which can be substituted in the alkyl radical by a group of the formula —$SO_2$—Y, where Y has the above meaning, or is an alkenoylamino group having 3 to 5 carbon atoms, such as the acryloylamino group, or is a benzoylamino group, which can be substituted by substituents from the group comprising chlorine, methyl, methoxy, nitro, sulfo, carboxy and —$SO_2$—Y, where Y has the above meaning, and is preferably the acetylamino or benzoylamino radical;

$R^6$ is a hydrogen atom or an alkyl group having 1 to 4 carbon atoms, an alkoxy group having 1 to 4 carbon atoms, a sulfo group, a carboxy group, a carbalkoxy group having 2 to 5 carbon atoms, a halogen atom, such as a bromine or chlorine atom, or an alkoxy group having 1 to 4 carbon atoms, which is substituted by a hydroxy, acetoxy, carboxy, carbamoyl or cyano group or a halogen atom, such as a chlorine atom;

$R^7$ is a hydrogen atom, an alkyl group having 1 to 4 carbon atoms, an alkoxy group having 1 to 4 carbon atoms, a halogen atom, such as a bromine or chlorine atom, the cyano group, the trifluoromethyl group or an alkoxy group having 1 to 4 carbon atoms, which is substituted by a hydroxy, acetoxy, carboxyl, carbamoyl or cyano group or by a halogen atom, such as a chlorine atom, or a group of the formula —$SO_2$—Y, where Y has the above meaning, or is an alkanoylamino group having 2 to 5 carbon atoms, which can be substituted by chlorine, bromine, alkoxy having 1 to 4 carbon atoms, phenoxy, phenyl, hydroxy, carboxy or sulfo or a group of the formula —$SO_2$—Y, where Y has the above meaning, or is an alkenoylamino group having 3 to 5 carbon atoms, which can be substituted by chlorine, bromine, carboxy or sulfo, or is the benzoylamino group, which can be substituted in the benzene nucleus, for example by substituents from the group comprising chlorine, methyl, sulfo and a group of the formula —$SO_2$—Y, where Y has the above meaning, or is an alkylsulfonyl group having 1 to 4 carbon atoms or the phenylsulfonyl group, which can be substituted in the benzene nucleus, for example by substituents from the group comprising chlorine, methyl, sulfo and a group of the formula —$SO_2$—Y, where Y has the above meaning, or is an alkylsulfonylamino group having 1 to 4 carbon atoms, which can be substituted by hydroxy, sulfato, chlorine, bromine, alkoxy having 1 to 4 carbon atoms or a group of the formula —$SO_2$—Y, where Y has the above meaning, or is the phenylsulfonylamino group, which can be substituted in the benzene nucleus, for example by substituents from the group comprising chlorine, methyl, sulfo and a group of the formula —$SO_2$—Y, where Y has the above meaning, or is the carbamoyl group, which can be mono- or disubstituted on the nitrogen atom by 1 or 2 substituents from the group comprising alkyl having 1 to 4 carbon atoms, alkyl having 1 to 4 carbon atoms which is substituted by, for example, hydroxy, sulfo, carboxy, sulfo or phenyl or a group of the formula —$SO_2$—Y, where Y has the above meaning, cycloalkyl having 5 to 8 carbon atoms, phenyl and phenyl which is substituted by substituents, for example from the group comprising chlorine, sulfo, methyl, methoxy, carboxy and a group of the formula —$SO_2$—Y, where Y has the above meaning, or is the sulfamoyl group, which can be mono- or disubstituted on the nitrogen atom by 1 or 2 substituents from the group comprising alkyl having 1 to 4 carbon atoms, alkyl having 1 to 4 carbon atoms which is substituted, for example by hydroxy, sulfo, carboxy, sulfato, phenyl or a group of the formula —$SO_2$—Y, where Y has the above meaning, cycloalkyl having 5 to 8 carbon atoms, phenyl and phenyl which is substituted by substituents, for example from the group comprising chlorine, sulfo, methyl, methoxy, carboxy and a group of the formula —$SO_2$—Y, where Y has the above meaning, or is the ureido group or a ureido group which can be mono- or disubstituted on the terminal nitrogen atom by 1 or 2 substituents from the group comprising alkyl having 1 to 4 carbon atoms, alkyl having 1 to 4 carbon atoms which is substituted by substituents, for example by hydroxy, sulfo, carboxy, sulfato, phenyl or a group of the formula —$SO_2$—Y, where Y has the above meaning, cycloalkyl having 5 to 8 carbon atoms, phenyl and phenyl which is substituted by substituents, for example from the group comprising chlorine, sulfo, methyl, methoxy, carboxy and a group of the formula —$SO_2$—Y, where Y has the above meaning;

$R^8$ is a hydrogen atom or an alkyl group having 1 to 4 carbon atoms, which can be substituted by, for example, hydroxy, sulfo, carboxy, sulfato, a group —$SO_2$—Y, where Y has the above meaning, or phenyl, or is an alkenyl group having 2 to 4 carbon atoms, which can be substituted by a carboxy or sulfo group or by a chlorine or bromine atom, or is a cycloalkyl radical having 5 to 8 carbon atoms;

$R^9$ is a hydrogen atom or an alkyl group having 1 to 4 carbon atoms, which can be substituted, for example by hydroxy, sulfo, carboxy, sulfato, phenyl or —$SO_2$—Y, where Y has the above meaning, or is an alkenyl group having 2 to 5 carbon atoms, which can be substituted by a carboxy or sulfo group or —$SO_2$—Y, where Y has the above meaning, or by a chlorine or bromine atom, or $R^9$ is a cycloalkyl radical having 5 to 8 carbon atoms or a phenyl radical, which can be substituted, for example by substituents from the group comprising chlorine, sulfo, methyl, methoxy, carboxy and —$SO_2$—Y, where Y has the above meaning, or $R^8$ and $R^9$, together with the nitrogen atom and optionally a further heteroatom, represent a saturated heterocyclic radical, such as, for example, the piperidino, morpholino or piperazino radical;

$R^{10}$ is a hydrogen atom or an alkyl group having 1 to 4 carbon atoms or an alkyl group having 1 to 4 carbon atoms which is substituted by alkoxy having 1 to 4 carbon atoms or cyano;

$R^{11}$ is a hydrogen atom or a sulfo group or a sulfoalkyl group with an alkylene radical having 1 to 4 carbon atoms, such as a sulfomethylene group, or a cyano or carbamoyl group;

$B^3$ is a hydrogen atom or an alkyl group having 1 to 6 carbon atoms, preferably 1 to 4 carbon atoms, which can be substituted by phenyl, sulfo, sulfophenyl or —$SO_2$—Y, where Y has the above meaning;

$B^4$ is a hydrogen atom, an alkyl group having 1 to 4 carbon atoms, an alkoxy group having 1 to 4 carbon atoms, such as a methoxy group, or an alkyl group having 1 to 4 carbon atoms which is substituted by a sulfo, carboxy, sulfato, acetylamino, benzoylamino or cyano group or a group of the formula —$SO_2$—Y, where Y has the above meaning, or is an alkenyl group having 2 to 4 carbon atoms, the cyclohexyl group, the phenyl group or a phenyl group which is substituted by substituents from the group comprising carboxy, sulfo, benzoylamino, acetylamino, —$SO_2$—Y, where Y has the above meaning, and chlorine;

k is the number zero or 1 (and in the case where k=zero, this group represents a hydrogen atom);

m represents the number 1 or 2;

$m_1$ represents the number 1, 2 or 3;

D* has one of the meanings given for the general formula (2), and here preferably the same meaning, or is a phenyl radical, which can be substituted by 1, 2 or 3, preferably 1 or 2, substituents from the group comprising alkyl having 1 to 4 carbon atoms, alkoxy having 1 to 4 carbon atoms, chlorine, bromine, hydroxy, carboxy, sulfo, carbamoyl, sulfamoyl and alkanoylamino, and of these preferably methyl, methoxy, ethoxy, chlorine, sulfo, carboxy and hydroxy, and/or by a group of the formula —$SO_2$—Y, where Y has the abovementioned meaning, and in which, preferably, one of these substituents is a sulfo or carboxy group and the group —$SO_2$—Y is preferably in the meta- or para-position relative to the azo group, or is a naphthyl radical, which is substituted by 1, 2 or 3 sulfo groups or by 1 or 2 sulfo groups and 1 or 2 groups of the general formula —$SO_2$—Y, where Y has the abovementioned meaning, or by only one such group —$SO_2$—Y, and in which D and D* can have meanings which are identical to one another or different from one another; K* is a radical from one of the abovementioned general formulae (4a) to (4m) which have been defined, and in which K and K* can have meanings which are identical to one another or different from one another;

W is a sulfo group or an alkylsulfonyl group having 1 to 4 carbon atoms or the phenylsulfonyl group or a bromine atom or preferably a fluorine or chlorine atom; and M has one of the abovementioned meanings.

The individual formula members can have meanings which are identical to one another or different from one another.

The free bonds which lead to the azo group in the above formulae (4e), (4f), (4g), (4h), (4i) and (4n), and the azo group in the formula (4p) and (4q) are attached in the ortho-position relative to the hydroxy or amino group. This hydroxy group is preferably bonded to the naphthalene radical in the α-position.

Alkyl groups having 1 to 4 carbon atoms are preferably the ethyl and in particular the methyl group; alkoxy groups having 1 to 4 carbon atoms are preferably the ethoxy and in particular the methoxy group; alkanoylamino groups having 2 to 5 carbon atoms are preferably the propionylamino group and in particular the acetylamino group, and carbalkoxy groups having 2 to 5 carbon atoms, are preferably the carbomethoxy and carbethoxy group.

Particularly preferred compounds of the general formula (1) according to the invention are those in which K is a radical of the general formula (4c), (4f), (4h), (4p) or (4q), in which in turn the individual formula members have the following preferred meanings:

$B^1$ is a carboxy or methyl group;

Q is a phenyl radical, which can be substituted by 1 or 2 substituents selected from the following group of substituents: 2 methyl, 2 methoxy, 1 chlorine or bromine, 2 sulfo, 1 carboxy and 1 vinylsulfonyl or β-sulfatoethylsulfonyl;

$R^5$ is the acetylamino or propionylamino group or a benzoylamino group, which can be substituted by 1 or 2 substituents from the group comprising chlorine, methyl, methoxy, nitro, sulfo or β-sulfatoethylsulfonyl; and R* and R" are both a hydrogen atom.

Particularly preferred compounds of the general formula (1) are those in which K represents the 1-hydroxynaphth-2-yl radical which is substituted by 1, 2 or 3 sulfo groups, or is a radical of the general formula (4c), in which $B^1$ is a carboxy or methyl group and Q represents a phenyl radical, which is substituted by 1 or 2 substituents selected from the group comprising 2 methyl groups, 2 ethoxy groups, 2 methoxy groups, 2 sulfo groups, 1 carboxy group and 1 chlorine atom, in which one of the substituents is necessarily a carboxy or sulfo group, or the phenyl radical is substituted by a vinylsulfonyl or β-sulfatoethylsulfonyl group and can additionally be substituted by 1 or 2 substituents selected from the group comprising 1 methyl, 2 methoxy, 1 chlorine and 1 sulfo.

In component K of the general formula (4v), $R^1$ is preferably a group —$SO_2$—Y, where Y has the abovementioned particularly preferred meaning, $R^2$ is a hydrogen atom, an alkyl group having 1 to 4 carbon atoms, an alkoxy group having 1 to 4 carbon atoms, a chlorine or bromine atom or a carboxy, sulfo or nitro group and $R^3$ is a hydrogen atom.

The present invention furthermore relates to processes for the preparation of the azo compounds of the general formula (1) according to the invention, for example by coupling reaction of the diazonium compound of an amino compound of the general formula (5)

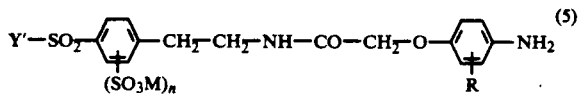

in which Y' has one of the meanings of Y or is the β-hydroxyethyl group and R, M and n have the abovementioned meanings, with a coupling component of the general formula H-K, where K has the abovementioned meaning; if K, as stated above, is a bivalent coupling component, a disazo compound can be prepared, if this is required, by reaction of this bivalent coupling component with twice the equimolar amount of the diazo component. If a compound (5) where Y' is a β-hydroxyethyl group is used, this β-hydroxyethyl group in the azo compound formed is converted into a group Y of the azo compound (1) according to the invention, as also stated below.

The diazotization and coupling reactions are carried out in the customary well-known manner, for ex. the diazotization of the amine (5) as a rule at a temperature between −5° C. and +15° C. and a pH below 2 by means of a strong acid and an alkali metal nitrite, preferably in an aqueous medium, and the coupling reaction is as a rule carried out at a pH between 1.5 and 4.5 in the case of a coupling component containing amino groups and at a pH between 3 and 7.5 in the case of a coupling component containing hydroxyl groups, and at a temperature between 0° C. and 30 C., preferably in an aqueous medium.

If the coupling component is a bivalent compound which can be coupled in two positions, for example if it contains an amino group which is capable of coupling and at the same time a hydroxy group which is capable of coupling, to prepare a disazo compound the coupling can first be carried out with the first mol of the diazonium compound of the amine in the acid pH range to give the monoazo compound, and the second coupling reaction can then be carried out with the second mol of the diazonium compound of the amine in the weakly acid to weakly alkaline range. This procedure applies, for example, to the compounds corresponding to the general formula (4p) and (4q), that is to say by first coupling the aminonaphtholsulfonic acid with the first mol of the diazonium compound of the amine of the general formula (5) or another aromatic amine corresponding to the general formula D*—$NH_2$, where D* has the abovementioned different meaning to D, in the acid medium and then by coupling the monoazo compound formed with the second mol of a diazonium compound of an amine D*—$NH_2$, where D* has the abovementioned meaning, in the weakly acid, neutral or weakly alkaline range, D* necessarily having one of the meanings given for D if the first coupling reaction has not been carried out with a diazonium compound of an amine (5), thus, in particular, initially at a pH of about 1 to 2.5 and then at a pH between 4 and 6.5, it being possible, if the diazonium compound of the amino compound (5) is identical in both coupling reactions, for the first and second coupling reaction to be carried out in one and the same batch, first in the acid range stated and then in the weakly acid to weakly alkaline range. To prepare a disazo compound corresponding to the general formula (4r) the reaction of the coupling component resorcinol with the diazonium compound or compounds is advantageously first carried out at a pH between 0.8 and 2 and then at a pH between 6 and 7.5.

Disazo compounds corresponding to the general formula (1), the radical K of which corresponds to the radical of an azo compound which is composed of a diazo component which is capable of coupling such as, for example, a radical corresponding to the general formula (4s) or (4t), can be prepared according to the invention by first coupling the diazonium compound of an amine (5) with the coupling component which contains an amino group and can thus be diazotized, such as, for example, in the formulae (4s) and (4t) the aniline and sulfo-aminonaphthalene components substituted by the substituents $R^6$ and $R^7$, diazotizing the amino group in the amino-azo compound thus formed and coupling the diazotization product with a coupling component, such as, for example, the coupling component H—K*, to give the disazo compound.

All these possible reactions with the synthesis of disazo compounds are analogous to the methods which are known in the literature or are familiar to the expert for the synthesis of disazo compounds.

Examples of coupling components which can be used for the preparation of the dyestuffs according to the invention and correspond, for example, to the general formulae (4a) to (4n) are: 1,3-diamino-benzene-5-sulfonic acid, phenol, cresol, resorcinol, 2-ethoxy-phenol, 4-methylphenol, 3-sulfophenol, salicylic acid, 3-sulfo-1-naphthol, 4-sulfo-1-naphthol, 5-sulfo-1-naphthol, 3,6-disulfo-8-naphthol, 4,6-disulfo-8-naphthol, 1-naphthol-3,8-disulfonic acid, 1-amino-8-naphthol-4-sulfonic acid, 1-amino-8-naphthol-5-sulfonic acid, 1-amino-8-naphthol-2,4-disulfonic acid, 2-amino-5-naphthol-7-sulfonic acid, 2-amino-5-naphthol-1,7-disulfonic acid, 1-amino-5-naphthol-7-sulfonic acid, 2-amino-8-naphthol-6-sulfonic acid, 2-amino-8-naphthol-3,6-disulfonic acid, 2-amino-8-naphthol-4,6-disulfonic acid, 1-amino-8-naphthol-3,6- or -4,6-disulfonic acid, 1-acryloylamino-8-naphthol-3,6-or -4,6-disulfonic acid, 1-propionylamino-8-naphthol-3,6- or -4,6-disulfonic acid, 1-acetylamino-8-naphthol-4-sulfonic acid, 1-acetylamino-8-naphthol-3,6-or -4,6-disulfonic acid, 1-benzoylamino-8-naphthol-3,6-or -4,6-disulfonic acid, 2-naphthol-5,7-disulfonic acid, 2-naphthol-3,6- and -6,8-disulfonic acid, 1,8-dihydroxynaphthalene-3,6-disulfonic acid, 1,8-dihydroxynaphthalene-6-sulfonic acid, 1naphthol-3,6,8-trisulfonic acid, 2-acetylamino-5-naphthol-7-sulfonic acid, 2-benzoylamino-8-naphthol-6-sulfonic acid, 2-(p'-tosylamino)-5-naphthol-7-sulfonic acid, 2-acetylamino-8-naphthol-3,6-disulfonic acid, 2-acetylamino-5-naphthol-1,7-disulfonic acid, 3-benzoylamino-8-naphthol-6-sulfonic acid, 2-phenylsulfonylamino-5-naphthol-7-sulfonic acid, 2-(N-methyl-N-acetyl)-amino-8-naphthol-6-sulfonic acid, N-ethyl-N-benzylaniline-3-sulfonic acid, N,N-bis-($\beta$-hydroxyethyl)-aniline, N,N-bis-($\beta$-sulfatoethyl)-aniline, N,N-bis-($\beta$-hydroxyethyl)-2-methoxy-5-chloro-aniline, N-($\beta$-sulfatoethyl)-2,5-dimethoxyaniline, N-($\beta$-sulfatoethyl)-2-chloroaniline, acetoacetyl-2-naphthylamide-5-sulfonic acid, N-acetoacetylaniline-3- or -4-sulfonic acid, N-acetoacetyl-2-methoxy-5-sulfo-aniline, N-acetoacetyl-4-methoxy-3-sulfoaniline, N-acetoacetyl-2-methoxy-5-methyl-4-sulfo-aniline, N-acetoacetyl-2,5-dimethoxy-4-sulfo-aniline, N-acetoacetyl-2-methoxy-5-methyl-4-($\beta$-sulfatoethylsulfonyl)-aniline, N-acetoacetyl-2,5-dimethoxy-4-($\beta$-sulfatoethylsulfonyl)-aniline, N-acetoacetyl-2-methoxy-5-($\beta$-sulfatoethylsulfonyl)-aniline, N-acetoacetyl-4-($\beta$-sulfatoethylsulfonyl)-aniline, N-acetoacetyl-3-($\beta$-sulfatoethylsulfonyl)-aniline, 1-(4'-$\beta$-sulfatoethylsulfonyl-phenyl)-3-methyl-pyrazol-5-one, 1-(4'-$\beta$-sulfatoethylsulfonyl-phenyl)-3-carboxy-pyrazol-5-one, 1-(4'-sulfophenyl)-3-methyl-pyrazol-5-one, 1-(4'-sulfophenyl)-3-carboxy-pyrazol-5-one, 1-(2'-chloro-5'-sulfo-phenyl)-3-methyl- or -3-carboxy-pyrazol-5-one, 1-(3'-sulfophenyl)-3-carboxypyrazol-5-one, 1-(2'-methoxy-4'-sulfophenyl)-3-carboxypyrazol-5-one, 1-(3'-sulfophenyl)-3-methyl-5-amino-pyrazole, 1-(4'-sulfo-phenyl)-3-methyl-5-aminopyrazole, 1-(2'-methoxy-5'-sulfophenyl)-3-methyl-5-aminopyrazole, 1-(2'-methoxy-5'-methyl-4'-sulfophenyl)-3-methyl-5-aminopyrazole, 1-(2'-chloro-5'-sulfo-phenyl)-3-methyl-5-aminopyrazole, 1-(3'-amino-4'-sulfo-phenyl)-3-carbethoxy-pyrazol-5-one, 1-(4'-$\beta$-sulfatoethylsulfonyl-phenyl)-3-carbethoxy-pyrazol-5-one, 1-(3'-amino-6'-methyl-phenyl)-3-carboxy-pyrazol-5-one, 2-N-methylamino-8-naphthol-6-sulfonic acid, 3-carboxypyrazol-5-one, 1-phenyl-3-carboxy-pyrazol-5-one, 1-(4'-nitrophenyl)-3-carboxypyrazol-5-one, 1-(3'-acetylaminophenyl)-3-carboxy-pyrazol-5-one, 1-(3'-carboxyphenyl)-3-methyl-pyrazol-5-one, 2-hydroxy-3-carboxy-naphthalene, 2-hydroxy-6-carboxy-naphthalene, 8-hydroxy-quinoline-5-sulfonic acid, 1,4-dimethyl-2-hydroxy-6-pyridone-5-sulfonic acid, N-sulfomethyl-aniline, 3-acetylamino-5-naphthol-7-sulfonic acid, 2-methylamino-8-naphthol-6-sulfonic acid, 2,5-disulfodiphenylamine, 4-sulfo-diphenylamine, 1-[4'-chloro-6'-(4''-$\beta$-sulfatoethylsulfonyl-phenyl)-amino-1',3',5'-triazin-2'-yl]-amino-8-naphthol-3,6-disulfonic acid, 1-[4'-chloro-6'-(4''-$\beta$-sulfatoethylsulfonyl-phenyl)-amino-1',3'-5'-triazin-2'-yl]-amino-8-naphthol-4,6-disulfonic acid, 2-[4'-chloro-6'-(4''-$\beta$-sulfataoethylsulfonyl-phenyl)-amino-1',3',5'-triazin-2'-yl]-amino-8-naphthol-6-sulfonic acid, 3-[4'-chloro-6'-(4''-$\beta$-sulfatoethylsulfonyl-phenyl)-amino-1',3',5'-triazin-2'-yl]-amino-8-naphthol-3,6-disulfonic acid, 1-(4'-chloro-6'-methoxy-1',3',5'-triazin-2'-yl)-amino-8-naphthol-3,6-disulfonic acid, 1-(4'-chloro-6'-methoxy-1',3',5'-triazin-2'-yl)-amino-8-naphthol-4,6-disulfonic acid, 2-(4'-chloro-6'-methoxy-1',3',5'-triazin-2'-yl)-amino-8-naphthol-6-sulfonic acid, 3-(4'-chloro-6'-methoxy-1',3',5'-triazin-2'-yl)-amino-8-naphthol-6-sulfonic acid, 1-[4'-fluoro-6'-(4''-$\beta$-sulfatoethylsulfonyl-phenyl)-amino-1',3',5'-triazin-2'-yl]-amino-8-naphthol-3,6-disulfonic acid, 1-[4'-fluoro-6'-(4''-$\beta$-sulfatoethylsulfonyl-phenyl)-amino-1',3',5'-triazin-2'-yl]-amino-8-naphthol-4,6-disulfonic acid, 2-[4'-fluoro-6'-(4''-$\beta$-sulfatoethylsulfonyl-phenyl)-amino-1',3',5'-triazin-2'-yl]-amino-8-naphthol-6-sulfonic acid, 3-[4'-fluoro-6'-(4''-$\beta$-sulfatoethylsulfonyl-phenyl)-amino-1',3',5'-triazin-2'-yl]-amino-8-naphthol-6-sulfonic acid, 1-(4'-$\beta$-sulfatoethylsulfonyl-benzoyl)-amino-8-naphthol-3,6-disulfonic acid or -4,6-disulfonic acid, 2- or 3-(4'-$\beta$-sulfatoethylsulfonyl-benzoyl)-amino-8-naphthol-6-sulfonic acid, 1-{4'-chloro-6'-[$\beta$-(4''-$\beta$''-sulfatoethylsulfonyl-phenyl)-ethyl]-1',3',5'-triazin-2'-yl}-amino-8-naphthol-3,6-or -4,6-disulfonic acid, 1-{4'-chloro-6'-[$\beta$-(3''-$\beta$''-sulfatoethylsulfonyl-phenyl)-ethyl]-1',3',5'-triazin-2'-yl]-amino-8-naphthol-3,6-or -4,6-disulfonic acid, 1-{4'-chloro-6'-[$\beta$-(4''-sulfo-phenyl)-ethyl]-1',3',5'-triazin-2'-yl}-amino-8-naphthol-3,6-or -4,6-disulfonic acid, 1-{4'chloro-6'-[$\beta$-(2'',5''-disulfophenyl)-ethyl]-1',3',5'-triazin-2'-yl}-amino-8-naphthol-3,6-or -4,6-disulfonic acid, 1-{4'-fluoro-6'-[$\beta$-(3'',5''-disulfophenyl)-ethyl]-1',3',5'-triazin-2'-yl}-amino-8-naphthol-3,6-or -4,6-disulfonic acid, 1-($\beta$-hydroxyethyl)-4-methyl-6-hydroxy-2-pyridone, 1-($\beta$-hydroxyethyl)-3-cyano-4-methyl-6-hydroxy-2-pyridone, 1-($\beta$-hydroxyethyl)-3-carbamoyl-4-methyl-6-hydroxy-2-pyridone, 1-($\beta$-hydroxyethyl)-4-methyl-6-hydroxy-2-pyridone-3-sulfonic acid, 1-($\beta$-sulfatoethyl)-4-methyl-6-hydroxy-2-pyridone, 1-($\beta$-sulfatoethyl)-3-cyano-4-methyl-6-hydroxy-2-pyridone, 1-($\beta$-sulfatoethyl)-3-carbamoyl-4-methyl-6-hydroxy-2-pyridone, 1-($\beta$-sulfatoethyl)-4-methyl-6-hydroxy-2-pyridone-3-sulfonic acid, 1-($\beta$-sulfatoethyl)-4-methyl-6-hydroxy-2-pyridone, 1-($\beta$-sulfatoethyl)-3-carbamoyl-4-methyl-6-hydroxy-2-pyridone, 1-($\beta$-sulfatoethyl)-4-methyl-6-hydroxy-2-pyridone-3-sulfonic acid, 1-carboxymethyl-4-methyl-6-hydroxy-2-pyridone, 1-carboxymethyl-3-cyano-4-methyl-6-hydroxy-2-pyridone, 1-carboxymethyl-3-carbamoyl-4-methyl-6-hydroxy-2-pyridone, 1-carboxymethyl-4-methyl-6-hydroxy-2-pyridone-3-sulfonic acid, 1-($\beta$-carboxyethyl)-4-methyl-6-hydroxy-2-pyridone, 1-($\beta$- carboxyethyl)-3-cyano-4-methyl-6-hydroxy-2-pyridone, 1-(β-carboxyethyl)-3-carbamoyl-4-methyl-6-hydroxy-2-pyridone, 1-(β-carboxyethyl)-4-methyl-6-hydroxy-2-pyridone-2-sulfonic acid, 1-(β-acetylaminoethyl)-4-methyl-6-hydroxy-2-pyridone, 1-(β-acetylaminoethyl)-3-cyano-4-methyl-6-hydroxy-2-pyridone, 1-(β-acetylaminoethyl)-3-carbamoyl-4-methyl-6-hydroxy-2-pyridone, 1-(β-acetylaminoethyl)-4-methyl-6-hydroxy-2-pyridone-3-sulfonic acid, 1-(β-acetylaminopropyl)-4-methyl-6-hydroxy-2-pyridone, 1-(β-acetylaminopropyl)-3-cyano-4-methyl-6-hydroxy-2-pyridone, 1-(β-acetylaminopropyl)-3-carbamoyl-4-methyl-6-hydroxy-2-pyridone, 1-(β-acetylaminopropyl)-4-methyl-6-hydroxy-2-pyridone-3-sulfonic acid, 4-hydroxy-2-quinoline, 1-amino-8-hydroxy-2-(phenylazo)-naphthalene-3,6-disulfonic acid, 1-amino-8-hydroxy-2-(4'-sulfophenylazo)-naphthalene-3,6-disulfonic acid, 1-amino-8-hydroxy-2-(2',5'-disulfophenylazo)-naphthalene-3,6-disulfonic acid, 1-(β-aminoethyl)-3-cyano-4-methyl-6-hydroxy-2-pyridone, 1-(γ-aminopropyl)-3-sulfomethyl-4-methyl-6-hydroxy-2-pyridone, 1,3-diaminobenzene, 1-amino-3-(N,N-di-β-hydroxyethylamino)-benzene, 1-amino-3-(N,N-di-β-sulfatoethylamino)-benzene, 1-amino-(3-N,N-di-β-hydroxyethylamino)-4-methoxybenzene, 1-amino-3-(N,N-di-β-sulfatoethylamino)-4-methoxy-benzene, 1-amino-3-(sulfobenzylamino)-benzene, 1-amino-3-(sulfobenzylamino)-4-chlorobenzene, 1-amino-3-(N,N-disulfobenzylamino)-benzene, phenol, 1-hydroxy-3- or -4-methylbenzene, 1-hydroxybenzene-4-sulfonic acid, 1-hydroxynaphthalene, 2-hydroxynaphthalene, 2-hydroxynaphthalene-6- or -7-sulfonic acid, 1-hydroxynaphthalene-4,7-disulfonic acid, 1-amino-3-methylbenzene, 1-amino-2-methoxy-5-methyl-benzene, 1-amino-2,5-dimethyl-benzene, 3-aminophenyl urea, 1-amino-3-acetylamino-benzene, 1-amino-3-(hydroxyacetylamino)-benzene, 1,3-diaminobenzene-4-sulfonic acid, 1-amino-naphthalene-6- or -8-sulfonic acid, 1-amino-2-methoxy-naphthalene-6-sulfonic acid, 2-aminonaphthalene-5,7-disulfonic acid, 1-amino-8-hydroxynaphthalene-6-sulfonic acid, 2-hydroxy-3-aminonaphthalene-5,7-disulfonic acid, 1-amino-8-hydroxy-naphthalene-2,4,6-trisulfonic acid, 1-hydroxy-8-acetylaminonaphthalene-3-sulfonic acid, 1-benzoylamino-8-hydroxynaphthalene-3,6-or -4,6-disulfonic acid, 2-benzoylamino-5-hydroxy-naphthalene-7-sulfonic acid, 2-methyl- and 2-ethylamino-5-hydroxy-naphthalene-7-sulfonic acid, 2-(N-acetyl-N-methylamino)-5-hydroxynaphthalene-7-sulfonic acid, 2-ethylamino-8-hydroxynaphthalene-6-sulfonic acid, 2-acetylamino-8-hydroxynaphthalene-6-sulfonic acid, 1-(4'-aminobenzoylamino)-8-hydroxynaphthalene-3,6-and -4,6-disulfonic acid, 1-(4'-nitrobenzoylamino)-8-hydroxynaphthalene-3,6-and -4,6-disulfonic acid, 1-(3'-aminobenzoylamino)-6-hydroxy-naphthalene-3,6-and -4,6-disulfonic acid, 1-(3'-nitrobenzoylamino)-8-hydroxy-naphthalene-3,6-and -4,6-disulfonic acid, 2-(4'-amino-3'-sulfophenyl)-amino-5-hydroxy-naphthalene-7-sulfonic acid, 3-methyl-5-pyrazolone, 1-phenyl-3-methyl-5-pyrazolone, 1-(3'-aminophenyl)-3-methyl-5-pyrazolone, 1-(2',5'-disulfophenyl)-3-methyl-5-pyrazolone, 1-(2'-methyl-4'-sulfophenyl)-5-pyrazolone-3-carboxylic acid, 1-(4'-8'-disulfonaphthyl-2'-yl)-3-methyl-5-pyrazolone, 1-(5',7'-disulfonaphthyl-2-)-3-methyl-5-pyrazolone, 1-(2',5'-dichloro-4'-sulfophenyl)-3-methyl-5-pyrazolone, 3-aminocarbonyl-4-methyl-6-hydroxy-2-pyridone, 1-ethyl-3-cyano or -3-chloro-4-methyl-6-hydroxy-2-pyridone, 1-ethyl-3-sulfomethyl-4-methyl-6-hydroxy-2-pyridone, 2,4,6-triamino-3-cyano-pyridine, 2-(3'-sulfophenyl)-amino-4,6-diamino-3-cyano-pyridine, 2-(2'-hydroxyethylamino)-3-cyano-4-methyl-6-amino-pyridine, 2,6-bis-(2'-hydroxyethylamino)-3-cyano-4-methylpyridine, 1-ethyl-3-carbamoyl-4-methyl-6-hydroxy-2-pyridone, 1-ethyl-3-sulfomethyl-4-methyl-5-carbamoyl-6-hydroxy-2-pyridone and N-acetoacetylamino-benzene.

The compounds corresponding to the general formula (5) which can be employed according to the invention for the synthesis of the azo compounds (1) according to the invention have not previously been disclosed. The invention thus also relates to these compounds, processes for their preparation and their use for the synthesis of dyestuffs, such as, in particular, to give the azo compounds (1) according to the invention. They can be prepared by procedures analogous to known procedures for the reaction of acid chlorides with amines, by first reacting a compound of the general formula (6)

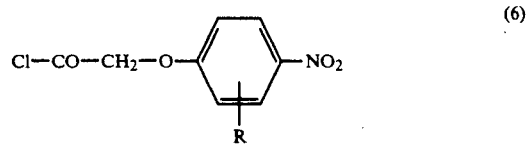

(6)

in which R has the abovementioned meaning, with an amino compound of the general formula

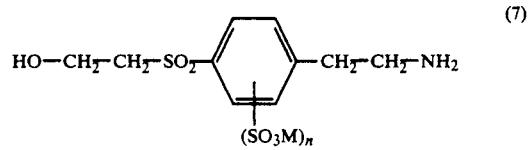

(7)

in which M and n have the abovementioned meanings. The reaction is carried out in the solvents or diluents which are customary and suitable for this reaction, in the presence of an acid-binding agent, as a rule at a temperature between 0° and 80° C. Examples of suitable solvents are water or an organic solvent or diluent or a mixture of water and a water-miscible organic solvent. Examples of organic solvents or diluents are water, alkanols having 1 to 6 carbon atoms, preferably 1 to 4 carbon atoms, such as, for example, methanol, dioxane, toluene, the xylenes, chlorobenzene, o-dichlorobenzene, m-dichlorobenzene, dimethylformamide and N-methyl-pyrrolidone.

Examples of acid-binding agents are potassium carbonate, magnesium oxide, sodium carbonate, sodium hydroxide, triethylamine and triethanolamine. In an aqueous medium, a pH between 6 and 12, preferably between 8 and 10, is maintained.

Examples of acid chlorides of the general formula (6) are 4-nitro-phenoxy-acetyl chloride, 2,4-dinitro-phenoxy-acetyl chloride, 2-chloro-4-nitro-phenoxy-acetyl chloride, 2-bromo-4-nitro-phenoxy-acetyl chloride, 2-methyl-4-nitro-phenoxy-acetyl chloride and 2-methoxy-4-nitro-phenoxy-acetyl chloride.

Amino compounds of the general formula (7) are, for example, 4-(β-hydroxyethylsufonyl)-1-(β-aminoethyl)-benzene, 5-(β-hydroxyethylsulfonyl)-2-(β-aminoethyl)-benzenesulfonic acid.

The carboxamide compounds according to the invention, corresponding to the general formula (8)

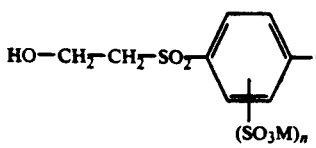 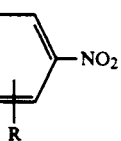 (8)

in which R, M and n have the abovementioned meanings, which are obtainable according to the invention in this manner and are likewise novel are then reduced, after they have been isolated from the reaction batch, for example, by crystallization or by distilling off the solvent or by acidification and filtration, to the amino compound corresponding to the general formula (5) by procedures analogous to known procedures, that is to say by catalytic hydrogenation with hydrogen over palladium, platinum or Raney nickel at a temperature between 50° and 110° C. and increased pressure or by Béchamp reduction with iron in an acid medium, for example with iron in ethanol/glacial acetic acid. The reduction can be carried out in a solvent which is suitable for this, such as water, methanol or ethanol or a mixture thereof.

Both the compounds corresponding to the general formula (1) and those of the general formula (5) in which Y or Y' is the β-hydroxyethyl group can be converted into compounds in which Y or Y' has a meaning other than the β-hydroxyethyl group by a customary and known procedure, thus, for example, into ester derivatives thereof, such as, for example, of polybasic inorganic acids or of aliphatic and aromatic carboxylic or sulfonic acids, thus, for example, in the compounds in which Y or Y' represents the β-chloroethyl, β-sulfatoethyl, β-phosphatoethyl, β-thiosulfatoethyl, β-acetoxyethyl or β-toluylsulfonyloxyethyl group. Examples of esterifying and acylating agents which are suitable for this are the corresponding inorganic or organic acids or anhydrides or halides or amides thereof, such as, for example, sulfuric acid, sulfuric acid containing sulfur trioxide, chlorosulfonic acid, amidosulfonic acid, phosphoric acid, phosphorus oxychloride, mixtures of phosphoric acid and phosphorus pentoxide, acetic anhydride, toluenesulfonyl chloride and thionyl chloride.

Those compounds in which Y or Y' represents the vinyl group can be prepared from analogous ester derivatives thereof by means of an alkali, thus in an aqueous medium at a pH of 10 to 12 and a temperature between 40 and 50° C. in the course of 10 to 20 minutes. The synthesis of, for example, β-(dialkylamino)-ethylsulfonyl and β-thiosulfatoethylsulfonyl derivatives of the compounds (1) and (5) is carried out by reaction of vinylsulfonyl compounds thereof with the corresponding dialkylamine or with an alkali metal salt of thiosulfuric acid, such as sodium thiosulfate. All these procedures for conversion of a group —$SO_2$—Y or —$SO_2$—Y' into another group are familiar to the expert in this fiber-reactive field and have been described in numerous instances in the literature.

The compounds of the general formula (1) according to the invention-called compounds (1) below-have fiberreactive properties and possess very useful dyestuff properties. They can therefore be used for dyeing (including printing) materials containing hydroxy groups and/or carboxamide groups. For this, the solutions obtained in the synthesis of the compounds (1) can be put to use in dyeing directly as the liquid preparation, if appropriate after addition of a buffer substance and if appropriate also after concentration.

The compounds (1) can be precipitated and isolated from the aqueous synthesis solutions by the generally known methods for water-soluble compounds, thus, for example, by precipitation from the reaction medium by means of an electrolyte, such as, for example, sodium chloride or potassium chloride, or by evaporation of the reaction solution itself, for example by spray drying. If the latter type of isolation is chosen, it is often advisable for any amounts of sulfate present in these solutions to be removed by precipitation as calcium sulfate and separation by filtration before the evaporation.

The present invention thus also relates to the use of the compounds (1) for dyeing (including printing) materials containing hydroxy and/or carboxamide groups and to processes for their use on these substrates. The materials are preferably used in the form of fiber materials, in particular in the form of textile fibers, such as yarns, wound packages and woven fabrics. Procedures analogous to known procedures can be followed here.

Materials containing hydroxy groups are those of natural or synthetic origin, such as, for example, cellulose fiber materials or regenerated products thereof, and polyvinyl alcohols. Cellulose fiber materials are preferably cotton, but also other plant fibers, such as linen, hemp, jute and ramie fibers; examples of the regenerated cellulose fibers are viscose staple and filament viscose.

Examples of materials containing carboxamide groups are synthetic and naturally occurring polyamides and polyurethanes, in particular in the form of fibers, for example wool and other animal hair, silk, leather, polyamide-6,6, polyamide-6, polyamide-11 and polyamide-4.

When used according to the invention, the compounds (1) can be applied to and fixed on the substrates mentioned, in particular on the fiber materials mentioned, by the use techniques known for water-soluble fiber-reactive dyestuffs, thus, for example, by applying the compound (1) in dissolved form to the substrate or incorporating it therein and fixing it on this or in this, if appropriate by the action of heat and/or if appropriate by the action of an alkaline agent. Such dyeing and fixing procedures are described in numerous instances in the literature (see, for example, European Patent Application Publication No. 0,181,585A2).

On cellulose fiber materials in particular, the dyeings according to the invention have good light-fastnesses both in the dry state of the dyeing and in the wet state, for example moistened with a perspiration solution, as well as good wet-fastnesses, such as, for example, good fastnesses to washing at 60° to 95° C., including in the presence of perborates, good fastnesses to acid and alkaline milling, cross-dyeing and perspiration, a high resistance to steam, good fastnesses to alkali, acid, water and sea water, and moreover a good fastness to pleating, fastness to ironing and fastness to rubbing. They likewise have a good resistance to storage in the presence of acid ("acid fading") on storage of moist dyed material which still contains acetic acid.

The following Examples serve to illustrate the invention. The part or parts by weight and the percentage data represent percentages by weight, unless noted otherwise. Parts by weight bear the same relationship to parts by volume as the kilogram to the liter.

The compounds described by the formulae in these Examples are shown in the form of the free acids; they are in general prepared and isolated in the form of their alkali metal salts, such as lithium, sodium or potassium salts, and used for dyeing in the form of their salts. The starting compounds and components mentioned in the form of the free acid in the following Examples, in particular the Tabular Examples, can likewise be employed in the synthesis as such or in the form of their salts, preferably alkali metal salts.

The absorption maxima ($\lambda_{max}$) in the visible range stated for the compounds according to the invention were determined with the aid of alkali metal salts thereof in aqueous solution. In the Tabular Examples, the $\lambda_{max}$ values are shown in parentheses where the color shade is shown; the wavelength data relate to nm.

EXAMPLE A

A solution of 237 parts of 4-nitrophenoxyacetyl chloride in 500 parts by volume of toluene is slowly added to a solution of pH 9 of 280 parts of β-[4-(β'-hydroxyethylsulfonyl)-phenyl]-ethylamine hydrochloride in about 1,500 parts of water at 5° to 10° C., while stirring thoroughly and maintaining the pH by means of about 3,000 parts of a 5% strength aqueous sodium hydroxide solution. The mixture is then subsequently stirred at 5° to 10° C. for about a further 4 hours and the product which has precipitated is filtered off with suction and recrystallized from methanol. It has the formula

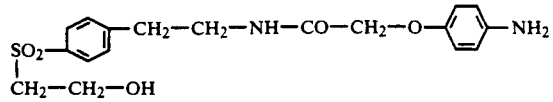

and has the following physical data:
Melting point: 113° C.;
Bands in the IR spectrum: 3352 cm$^{-1}$ (NH); 2928 cm$^{-1}$ (CH); 1655 cm$^{-1}$ (CO);
Elemental analysis (C$_{18}$H$_{20}$N$_2$O$_7$S): calculated: C 52.9%; H 4.9%; N 6.8%; S 7.8%. found: C 52.7%; H 4.9%; N 6.7%; S 7.6%.

EXAMPLE B 56 parts of nitro compound of Example A are suspended in 300 parts of methanol and reduced by means of hydrogen over Raney nickel at a temperature of 60° C. under a hydrogen pressure of 60 bar. When the reaction has ended, the catalyst is removed by filtration at 90° C. and the filtrate is allowed to cool to 20° C. The product which has crystallized out is filtered off with suction and rinsed with 100 parts of methanol. It has the formula

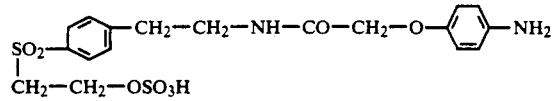

and has the following physical data:
Melting point: 136° C.;
Bands in the IR spectrum: 3376 cm$^{-1}$ (NH); 3300 cm$^{-1}$ (NH); 2960 cm$^{-1}$ (CH); 1655 cm$^{-1}$ (CO).

EXAMPLE C 37 parts of the aniline compound of Example B are introduced into 148 parts of sulfuric acid monohydrate at 10° C. The resulting suspension is then heated slowly to 20° C., stirred further for another 3 hours and then poured onto 1,600 parts of ice and the precipitate is filtered off with suction.

The compound has the formula

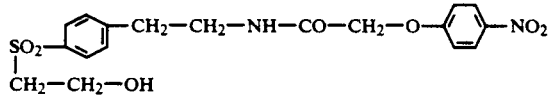

and shows the following bands in the IR spectrum: 3390 cm$^{-1}$ (NH); 2944 cm$^{-1}$ (CH); 1660 cm$^{-1}$ (CO).

EXAMPLE 1

First 20 parts of an aqueous 5 N sodium nitrite solution and then, at 5° C., 70 parts of an aqueous concentrated hydrochloric acid are added to an aqueous solution of pH 6.8 of 64.8 parts of the aniline compound of Example C in 3,200 parts of water. When the diazotization reaction has ended, excess nitrite is removed with amidosulfonic acid, 51 parts of 1-acetylamino-8-naphthol-3,6-disulfonic acid are added to the diazonium salt suspension at 5° C., while maintaining a pH of 6, the mixture is then subsequently stirred at 15° to 20° C. for about a further 24 hours, the pH is brought to 4.5 to 5 and the azo compound according to the invention is isolated by salting out with sodium chloride and filtration. It has the formula, written in the form of the free acid,

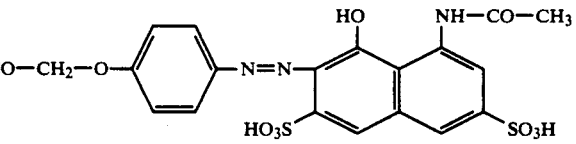

($\lambda_{max}$ = 547 nm)

and has very good fiber-reactive dyestuff properties. When used by the application and fixing processes known for fiber-reactive dyestuffs, the azo compound according to the invention gives deep bluish-tinged red dyeings and prints with good fastness properties on the materials mentioned in the description, such as, in particular, cellulose fiber materials, for example cotton.

EXAMPLES 2 to 52

Other azo compounds according to the invention corresponding to the general formula (A), written in the form of the free acid

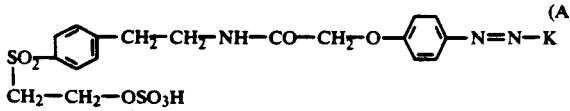

are described with the aid of their coupling component H-K in the following Tabular Examples. They can be prepared in the manner according to the invention, for example analogously to the above Example 1, and likewise have very good fiber-reactive dyestuff properties. On the materials mentioned in the description, such as, in particular, cellulose fiber materials, they produce deep dyeings and prints having the color shade stated in the particular Tabular Example (on cotton here) with good fastness properties by the application and fixing methods customary for fiber-reactive dyestuffs; the values stated in parentheses are the absorption maxima ($\lambda_{max}$) in nm.

| Example | Coupling component H-K in formula (A) | Colour shade |
|---|---|---|
| 2 | 6-sulfo-3-benzoylamino-8-naphthol | red |
| 3 | 1-(4'-β-sulfatoethylsulfonyl-phenyl)-3-methyl-5-pyrazolone | yellow (419) |
| 4 | 4,6-disulfo-1-acetylamino-8-naphthol | bluish-tinged red (547) |
| 5 | 3,6-disulfo-2-amino-naphthalene | red |
| 6 | 5,7-disulfo-2-amino-naphthalene | navy/blue |
| 7 | 4-sulfo-1-naphthol | red |
| 8 | 3,6-disulfo-1-naphthol | red |
| 9 | 1-(N-β-sulfoethyl)-4-methyl-2-hydroxy-6-pyridone | orange |
| 10 | 3,6,8-trisulfo-2-amino-naphthalene | red |
| 11 | 6-sulfo-3-acetylamino-8-naphthol | red (499) |
| 12 | N,N-bis-(β-sulfatoethyl)-aniline | orange |
| 13 | N-ethyl-N-(β-sulfatoethyl)-aniline | red |
| 14 | 6-sulfo-2-acetylamino-8-naphthol | red (509) |
| 15 | 3,6-disulfo-1-benzoylamino-8-naphthol | bluish-tinged red (551) |
| 16 | 4,6-disulfo-1-benzoylamino-8-naphthol | bluish-tinged red |
| 17 | N,N-bis-(β-sulfatoethyl)-3-chloro-aniline | orange |
| 18 | 5-sulfo-1-naphthol | red |
| 19 | 3,6-disulfo-1-amino-2-{2'-sulfo-5'-[5''-(β-sulfatoethylsulfonyl)-1'',2'',3''-benzotriazol-1''-yl]-phenyl-diazoyl}-8-naphthol | greenish-tinged blue |
| 20 | 3,6-disulfo-1-amino-2-[4'-(β-sulfatoethylsulfonyl)-phenyl-diazoyl]-8-naphthol (627) | greenish-tinged blue |
| 21 | 6-sulfo-2-methylamino-8-naphthol | red |
| 22 | 4-sulfo-diphenylamine | red |
| 23 | 5-sulfo-2-acetylamino-7-naphthol | red |
| 24 | 3,6-disulfo-2-acetylamino-8-naphthol | red |
| 25 | 2,4-disulfo-1-amino-8-naphthol | blue |
| 26 | 3,6-disulfo-1-amino-8-naphthol (coupled in the 7-position) | blue |
| 27 | 4,6-disulfo-1-amino-8-naphthol (coupled in the 7-position) | blue |
| 28 | 3,6-disulfo-1-phenylureido-8-naphthol | blue |
| 29 | 3-sulfo-1-naphthol | red |
| 30 | 5-sulfo-2-naphthol | red |
| 31 | 6-sulfo-2-naphthol | bluish-tinged red |
| 32 | 8-sulfo-2-naphthol | bluish-tinged red |
| 33 | 3,6-disulfo-1-acetylamino-8-naphthol | blue |
| 34 | N,N-bis-(β-hydroxyethyl)-aniline | red |
| 35 | 3,6,8-trisulfo-1-naphthol | bluish-tinged red |
| 36 | 3,6-disulfo-2-naphthol | red |
| 37 | 3,6-disulfo-1-acetylamino-8-naphthol | blue |
| 38 | 4,6-disulfo-1-acetylamino-8-naphthol | blue |
| 39 | N-ethyl-N-(3'-sulfobenzyl)-aniline | red |
| 40 | 5-sulfo-1,4-dimethyl-2-hydroxy-6-pyridone | yellow |
| 41 | 2-carboxy-acetoacetylaniline | yellow |
| 42 | 5-sulfo-8-hydroxy-quinoline | red |
| 43 | 3-sulfo-acetoacetylaniline | yellow |
| 44 | 1-(4'-sulfophenyl)-3-methyl-5-pyrazolone | yellow (416) |
| 45 | 1-(2'-chloro-5'-sulfophenyl)-3-methyl-5-pyrazolone | yellow |
| 46 | 1-(2',5'-disulfophenyl)-3-methyl-5-pyrazolone | yellow |
| 47 | 1-(4',8'-disulfo-naphth-2'-yl)-3-methyl-5-pyrazolone | yellow |
| 48 | 1-(4'-sulfophenyl)-3-methyl-5-aminopyrazole | yellow |
| 49 | 3,6-disulfo-1-[4'-chloro-6'-(3''-sulfophenyl)-amino-1',3',5'-triazine-2'-yl]-amino-8-naphthol | bluish-tinged red |
| 50 | 3,6-disulfo-1-{4'-chloro-6'-[4''-(β-sulfatoethylsulfonyl)-phenyl]-amino-1',3',5'-triazine-2'-yl}-amino-8-naphthol | bluish-tinged red (555) |
| 51 | 6,8-disulfo-2-naphthol | red |
| 52 | 6-sulfo-2-benzoylamino-8-naphthol | red |

We claim:

1. A water-soluble azo compound corresponding to the formula $$D-N=N-K$$

in which:

D is a group of the formula $$Y-SO_2-\underset{(SO_3M)_n}{\underset{|}{\bigcirc}}-CH_2-CH_2-NH-CO-CH_2-O-\underset{R}{\bigcirc}-$$

in which:

Y is vinyl or a group of the formula —CH₂—CH₂—X in which X is a substituent which is eliminated by an alkali while forming the vinyl, R is hydrogen, nitro, alkyl of 1 to 4 carbons, alkoxy of 1 to 4 carbons, carboxy, hydroxy or halogen, n is zero or 1, and M is hydrogen or an alkali-metal, and K is a group of the formula $$\underset{CO-NH}{\overset{CO-CH_3}{\underset{|}{-CH}}}-\underset{R^3 \quad R^1}{\bigcirc}^{R^2} \quad \text{or}$$

-continued

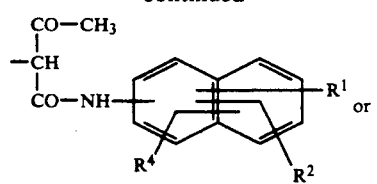
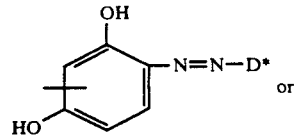
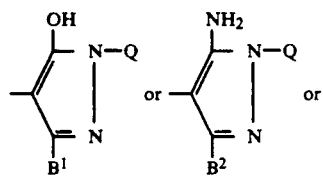
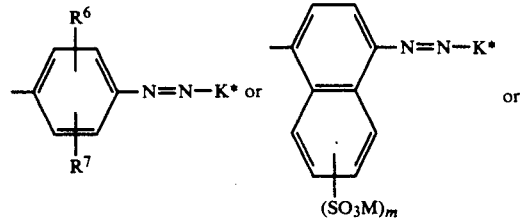
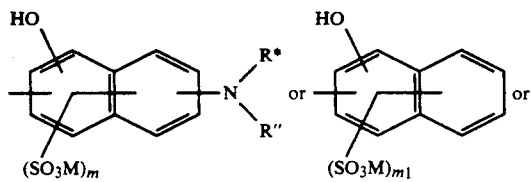
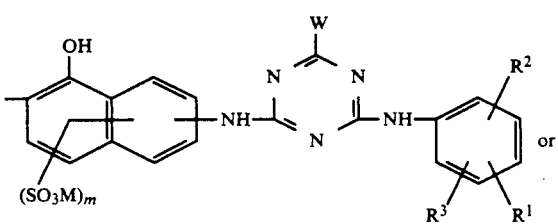
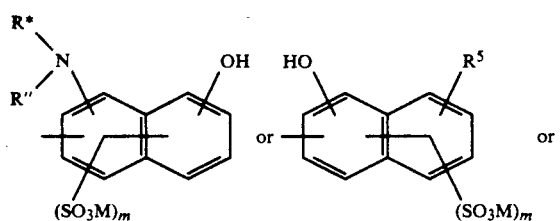
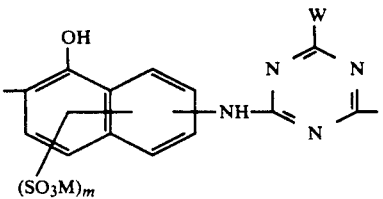
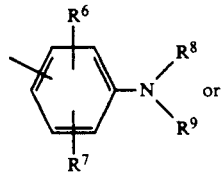
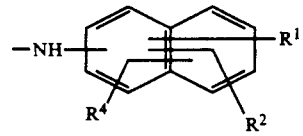
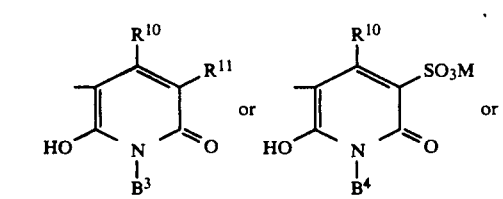
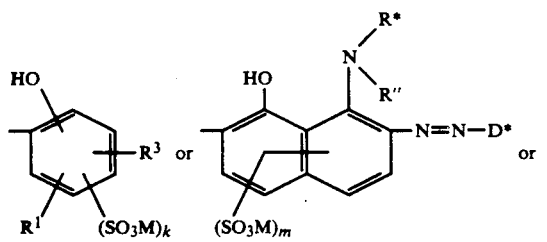
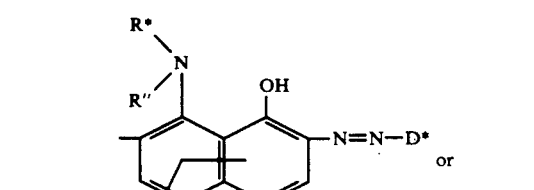

in which

R¹ is hydrogen, carboxy, sulfo, or a group of the formula —SO₂—Y;

R² is hydrogen, alkyl of 1 to 4 carbons, alkoxy of 1 to 4 carbons, chlorine, bromine, carboxy, sulfo, or nitro;

R³ is hydrogen, alkyl of 1 to 4 carbons, alkoxy of 1 to 4 carbons, chlorine, or bromine;

R⁴ is hydrogen, sulfo, or carboxy;

B¹ is alkyl of 1 to 4 carbons, carboxy, carbalkoxy of 2 to 5 carbons, —CONH₂, or phenyl, which is unsubstituted or substituted by substituents selected from sulfo, carboxy, methyl, ethyl, methoxy, ethoxy, and chlorine;

B² is alkyl of 1 to 4 carbons, carboxy, carbalkoxy of 2 to 5 carbons, —CONH₂, or phenyl, which is unsubstituted or substituted by 1 or 2 substituents selected from alkyl of 1 to 4 carbons, alkoxy of 1 to 4 carbons, chlorine, bromine, or sulfo;

Q is phenyl, which is unsubstituted or substituted by one, two, or three substituents selected from chlorine, bromine, methyl, ethyl, methoxy, ethoxy, carboxy, sulfo, acetylamino, and a group of the formula —SO₂—Y, or is a naphthyl, which is unsubstituted or substituted by one, two, or three sulfos, or by an alkyl of 1 to 4 carbons, an alkoxy of 1 to 4 carbons, a chlorine, or an alkanoylamino of 2 to 5 carbons, or by a group of the formula —SO$_2$—Y, or is naphthyl substituted by one, two or three sulfos and by a group selected from alkyl of 1 to 4 carbons, alkoxy of 1 to 4 carbons, chlorine, alkanoylamino of 2 to 5 carbons and a group of the formula —SO$_2$—Y;

R* is hydrogen, or alkyl or 1 to 4 carbons, which is unsubstituted or substituted by a phenyl which is further unsubstituted or substituted by sulfo, or by —SO$_2$—Y, or by sulfo and —SO$_2$—Y R'' is hydrogen, or alkyl or 1 to 4 carbons which is unsubstituted or substituted by phenyl, or by a group of the formula —SO$_2$—Y, or is phenyl which is unsubstituted or substituted by one or two substituents selected from alkyl of 1 to 4 carbons, alkoxy of 1 to 4 carbons, chlorine, bromine, sulfo, and —SO$_2$—Y;

R$^5$ is phenylureido wherein the phenyl is unsubstituted or substituted by a group of the formula —SO$_2$—Y, or is alkanoylamino of 2 to 5 carbons which is unsubstituted or substituted in the alkyl moiety by a group of the formula —SO$_2$—Y, or is alkenoylamino of 3 to 5 carbons or is benzoylamino which is unsubstituted or substituted by substituents selected from chlorine, methyl, methoxy, nitro, sulfo, carboxy, and a group of the formula —SO$_2$—Y;

R$^6$ is hydrogen, alkyl of 1 to 4 carbons, alkoxy of 1 to 4 carbons, sulfo, carboxy, carbalkoxy of 2 to 5 carbons, halogen or alkoxy of 1 to 4 carbons substituted by hydroxy, acetoxy, carboxy, —CONH$_2$, cyano, or halogen;

R$^7$ is hydrogen, alkyl of 1 to 4 carbons, alkoxy of 1 to 4 carbons, halogen, cyano, trifluoromethyl or alkoxy of 1 to 4 carbons substituted by hydroxy, acetoxy, carboxy, —CONH$_2$, cyano, halogen, or a group of the formula —SO$_2$—Y, or is alkanoylamino of 2 to 5 carbons which is unsubstituted or substituted by chlorine, bromine, alkoxy of 1 to 4 carbons, phenoxy, phenyl, hydroxy, carboxy, sulfo, or a group of the formula —SO$_2$—Y, or is alkenoylamino of 3 to 5 carbons, which is unsubstituted or substituted by chlorine, bromine, carboxy or sulfo, or is benzoylamino which is unsubstituted or substituted in the benzene ring by substituents selected from chlorine, methyl, sulfo, and a group of the formula —SO$_2$—Y, or is alkylsulfonyl of 1 to 4 carbons or is phenylsulfonyl which is unsubstituted or substituted in the phenyl by substituents selected from chlorine, methyl, sulfo, and a group of the formula —SO$_2$—Y, or is alkylsulfonylamino of 1 to 4 carbons, which is unsubstituted or substituted by hydroxy, sulfato, chlorine, bromine, alkoxy of 1 to 4 carbons or a group of the formula —SO$_2$—Y, or is phenylsulfonylamino, which is unsubstituted or substituted in the phenyl by substituents selected from chlorine, methyl, sulfo, and a group of the formula —SO$_2$—Y, or is —CONH$_2$, which is unsubstituted or mono- or disubstituted on the nitrogen by one or two substituents selected from the group: alkyl of 1 to 4 carbons; alkyl of 1 to 4 carbons substituted by hydroxy, sulfo, carboxy, sulfato, phenyl, or a group of the formula —SO$_2$—Y; cycloalkyl of 5 to 8 carbons, phenyl, which is unsubstituted or substituted by substituents selected from chlorine, sulfo, methyl, methoxy, carboxy, and a group of the formula —SO$_2$—Y; or is sulfamoyl, which is unsubstituted or mono- or disubstituted on the nitrogen by one or two substituents selected from the group consisting of: alkyl of 1 to 4 carbons; alkyl of 1 to 4 carbons substituted by hydroxy, sulfo, carboxy, sulfato, phenyl, or a group of the formula —SO$_2$—Y, cycloalkyl of 5 to 8 carbons; phenyl, which is unsubstituted or substituted by substituents selected from chlorine, sulfo, methyl, methoxy, carboxy, and a group of the formula —SO$_2$—Y; or is ureido, which is unsubstituted or mono- or disubstituted on the terminal nitrogen by one or two substituents from the group consisting of: alkyl or 1 to 4 carbons, alkyl of 1 to 4 carbons substituted by substituents selected from hydroxy, sulfo, carboxy, sulfato, phenyl, or a group of the formula —SO$_2$—Y; cycloalkyl of 5 to 8 carbons; phenyl, which is unsubstituted or substituted by substituents selected from the group consisting of chlorine, sulfo, methyl, methoxy, carboxy, and a group of the formula —SO$_2$—Y;

R$^8$ is hydrogen, alkyl of 1 to 4 carbons, or alkyl or 1 to 4 carbons substituted by hydroxy, sulfo, carboxy, sulfato, a group of the formula —SO$_2$—Y, or by phenyl, or is alkenyl of 2 to 4 carbons which is unsubstituted or substituted by carboxy, sulfo, chlorine or bromine, or is cycloalkyl or 5 to 8 carbons;

R$^9$ is hydrogen, or alkyl of 1 to 4 carbons or alkyl or 1 to 4 carbons which is unsubstituted or substituted by hydroxy, sulfo, carboxy, sulfato, phenyl, or a group of the formula —SO$_2$—Y, or is alkenyl of 2 to 5 carbons which is unsubstituted or substituted by carboxy, sulfo, a group of the formula —SO$_2$—Y, chlorine, or bromine, or is cycloalkyl of 5 to 8 carbons or phenyl, which is unsubstituted or substituted by substituents selected from chlorine, sulfo, methyl, methoxy, carboxy, and a group of the formula —SO$_2$—Y, or R$^8$ and R$^9$ represent together with the nitrogen piperidino, morpholino or piperazino;

R$^{10}$ is hydrogen, or alkyl of 1 to 4 carbons which is unsubstituted or substituted by alkoxy of 1 to 4 carbons or by cyano;

R$^{11}$ is hydrogen, sulfo, sulfoalkyl with an alkyl moiety or 2 to 5 carbons, cyano, or —CONH$_2$;

B$^3$ is hydrogen, or alkyl or 1 to 6 carbons which is unsubstituted or substituted by phenyl, sulfo, sulfophenyl, or a group of the formula —SO$_2$—Y;

B$^4$ is hydrogen, alkoxy of 1 to 4 carbons, alkyl or 1 to 4 carbons, which is unsubstituted or substituted by sulfo, carboxy, sulfato, acetylamino, benzoylamino, cyano, or a group of the formula SO$_2$—Y, or is alkenyl of 2 to 4 carbons, cyclohexyl, phenyl, which is unsubstituted or substituted by substituents selected from carboxy, sulfo, benzoylamino, acetylamino, a group of the formula —SO2—Y, and chlorine;

K is zero or 1 (and in the case where K is zero, this group is hydrogen);

m is 1 or 2;

m$_1$ is 1, 2 or 3;

W is sulfo, alkylsulfonyl or 1 to 4 carbons, phenylsulfonyl, bromine, fluorine or chlorine;

D* is a group of the formula

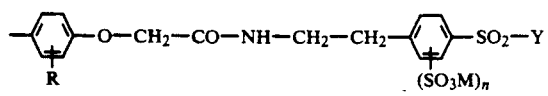

in which R, Y and M and n are as defined above, or D* is phenyl, which is unsubstituted or substituted by 1, 2, or 3 substituents selected from alkyl of 1 to 4 carbons, alkoxy of 1 to 4 carbons, chlorine, bromine, hydroxy, carboxy, sulfo, —$CONH_2$ and —$SO_2NH_2$, and alkanoylamino of 2 to 5 carbons, or a group of the formula —$SO_2$—Y, or by a combination of those substituents, or is naphthyl, which is unsubstituted or substituted by 1, 2 or 3 sulfos, or by 1 or 2 sulfos and 1 or 2 groups of the formula —$SO_2$—Y, or by one group —$SO_2$—Y;

K* is a group of the formula

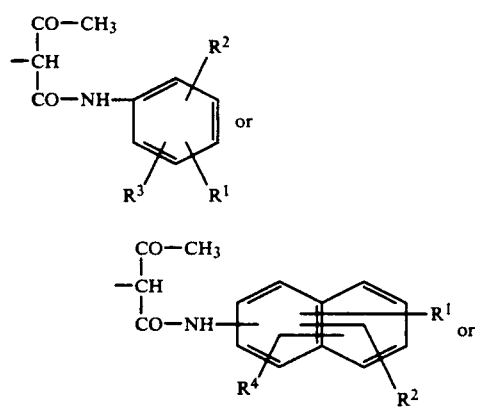

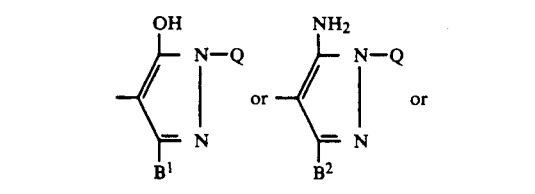

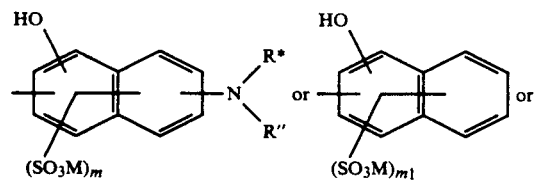

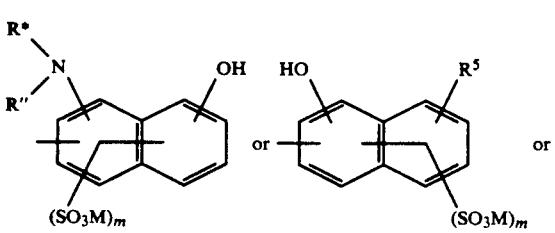

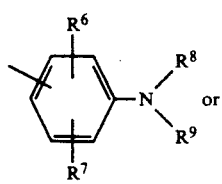

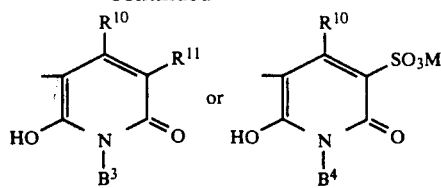

2. A compound as claimed in claim 1, in which K is a group of the formula

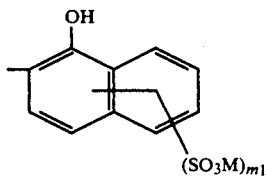

in which $m_1$ represents the number 1, 2 or 3.

3. A compound as claimed in claim 1, in which K is a group of the formula

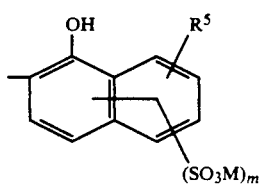

in which $R^5$ is benzoylamino or an alkanoylamino having 2 to 5 carbons and m represents the number 1 or 2.

4. A compound as claimed in claim 1, in which K is a group of the formula

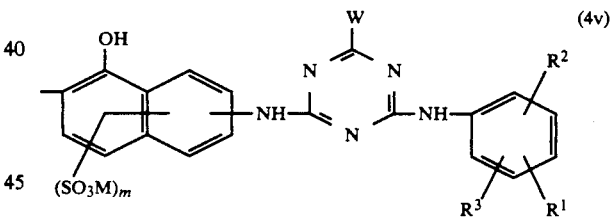
(4v)

in which m represents the number 1 or 2, W is sulfo alkylsulfonyl having 1 to 4 carbons, phenylsulfonyl, bromine, fluorine, or chlorine, $R^1$ is the group —$SO_2$—Y, $R^2$ is hydrogen, alkyl having 1 to 4 carbons, alkoxy having 1 to 4 carbons, chlorine, bromine, carboxy, sulfo or nitro and $R^3$ denotes hydrogen.

5. A compound as claimed in claim 1, in which K is a group of the formula

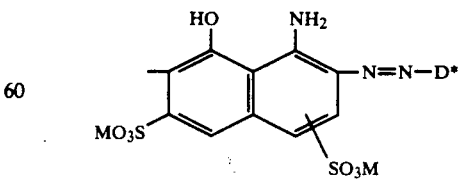

in which D* is phenyl, which is unsubstituted or substituted by 1, 2 or 3 substituents, selected from alkyl having 1 to 4 carbons, alkoxy having 1 to 4 carbons, chlorine, bromine, hydroxy, carboxy, sulfo, —$CONH_2$, —$SO_2NH_2$ alkanoylamino having 2 to 5 carbons, or a group of the formula —SO$_2$—Y, or mixtures thereof, or D* is naphthyl, which is unsubstituted or substituted by 1, 2 or 3 sulfos, by 1 or 2 sulfos and 1 or 2 groups of the formula —SO$_2$—Y, or by one group —SO$_2$—Y.

6. A compound as claimed in claim 4, in which W is a fluorine or chlorine.

7. A compound as claimed in claim 5, in which D* is phenyl which is unsubstituted or substituted in the para-position relative to the azo by a group of the formula —SO$_2$—Y is the vinyl group or a group of the formula —CH$_2$—CH$_2$—X in which X is a substituent which can be eliminated by an alkali to form the vinyl group.

8. A compound as claimed in claim 1, in which n represents the number zero.

9. A compound as claimed in claim 1, in which R is hydrogen.

10. A compound as claimed in claim 1, in which Y represents vinyl, or β-sulfatoethyl 11. A compound as claimed in claim 1, in which Y is β-sulfatoethyl.

12. A compound as claimed in claim 1, in which M represents hydrogen or an alkali metal.

* * * * *